United States Patent
Rhee et al.

Patent Number: 6,093,836
Date of Patent: Jul. 25, 2000

[54] 1,3-DIPHENYLPROPANE DERIVATIVES HAVING INHIBITORY ACTIVITY AGAINST TYROSINASE AND PROCESS FOR PREPARATION THEREOF

[75] Inventors: Young Ho Rhee; Kyung Ae Kim; Hyun Ho Lee; Jong Kwon Choi; Sang Hwa Lee, all of Daejeon, Rep. of Korea

[73] Assignee: LG Chemical Ltd., Seoul, Rep. of Korea

[21] Appl. No.: 09/180,352

[22] PCT Filed: Mar. 2, 1998

[86] PCT No.: PCT/KR98/00039

§ 371 Date: Nov. 6, 1998

§ 102(e) Date: Nov. 6, 1998

[87] PCT Pub. No.: WO98/39279

PCT Pub. Date: Sep. 11, 1998

[30] Foreign Application Priority Data

Mar. 6, 1997 [KR] Rep. of Korea ............ 97/7452

[51] Int. Cl.[7] ............ C07C 43/205; C07C 49/303; C07C 49/603; C07D 311/58
[52] U.S. Cl. ............ 549/405; 549/413; 549/408; 568/367; 568/664
[58] Field of Search ............ 549/408, 405, 549/413; 568/367, 664

[56] References Cited

FOREIGN PATENT DOCUMENTS

| | | |
|---|---|---|
| 0112587 | 7/1984 | European Pat. Off. . |
| 0292576 | 11/1988 | European Pat. Off. . |
| 0721930 | 7/1996 | European Pat. Off. . |
| 2258304 | 7/1973 | Germany . |
| WO 9105757 | 5/1991 | WIPO . |
| WO 9414477 | 7/1994 | WIPO . |
| WO 9116293 | 10/1994 | WIPO . |

*Primary Examiner*—Joseph McKane
*Assistant Examiner*—Taofiq A. Solola
*Attorney, Agent, or Firm*—Birch, Stewart, Kolasch & Birch, LLP

[57] ABSTRACT

The present invention relates to a novel 1,3-diphenylpropane derivative having an inhibitory activity against tyrosinase represented by the following formula (I):

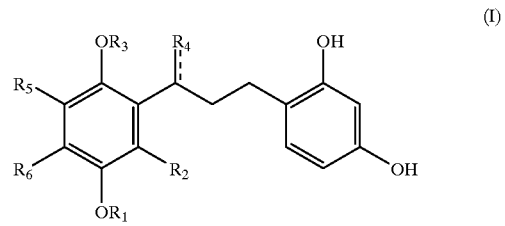

in which
- - - represents double or single bond,
$R_1$ represents hydrogen or $C_1$–$C_{10}$ alkyl,
$R_2$ represents $C_1$–$C_5$ alkyl or $C_1$–$C_5$ alkoxyalkyl, or
$R_1$ and $R_2$ together represent a 5 to 6 membered heterocycle which can be substituted by $C_1$–$C_5$ alkyl and which contains oxygen as the hetero atom,
$R_3$ represents hydrogen or $C_1$–$C_7$ alkyl,
$R_4$ represents hydrogen, hydroxy, or oxo, and
$R_5$ and $R_6$ mindependently of one another represent hydrogen or $C_1$–$C_5$ alkyl.

14 Claims, No Drawings

1,3-DIPHENYLPROPANE DERIVATIVES HAVING INHIBITORY ACTIVITY AGAINST TYROSINASE AND PROCESS FOR PREPARATION THEREOF

This application is the national phase under 35 U.S.C. §371 of prior PCT International Application No. PCT/KR98/00039 which has an International filing date of Mar. 2, 1998 which designated the United States of America, the entire contents of which are hereby incorporated by reference.

TECHNICAL FIELD

The present invention relates to a novel 1,3-diphenylpropane derivative having an inhibitory activity against tyrosinase represented by the following formula (I):

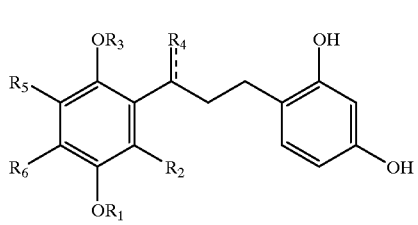

in which
- -- represents double or single bond,
- $R_1$ represents hydrogen or $C_1$–Clo alkyl,
- $R_2$ represents $C_1$–$C_5$ alkyl or $C_1$–$C_5$ alkoxyalkyl, or
- $R_1$ and $R_2$ together represent a 5 to 6 membered heterocycle which can be substituted by $C_1$–$C_5$ alkyl and which contains oxygen as the hetero atom,
- $R_3$ represents hydrogen or $C_1$–$C_7$ alkyl,
- $R_4$ represents hydrogen, hydroxy, or oxo, and
- $R_5$ and $R_6$ independently of one another represent hydrogen or $C_1$–$C_5$ alkyl.

The present invention also relates to novel processes for preparation of the compound of formula (I) as defined above.

BACKGROUND ART

Melanin is prepared through the conversion of Tyrosine into DOPA, Dopaquinone by the action of Tyrosinase located in the chromatophore then through the non-enzymatic oxidation. Melanin is distributed over the skin and has an important function to protect the body from various stimuli. However, it has been reported that excess production of melanin is closely related to melanoma and may also induce melanistic skin freckles, etc. Accordingly, a variety of cosmetics and medicaments for the prevention of excess production of melanin are actively developed in these days.

As the preventive agent for the excess production of melanin, hydroquinone has been mainly used heretofore. This compound, however, also exhibits side effects such as degeneration or lethal mutation of melanin, damage of the cellular function, etc., and therefore the use of hydroquinone in cosmetics is now prohibited in Korea, Japan, etc.(see, J. Soc. Cosmet. Chem., 42, 361, 1991). In addition, arbutin, a sugar derivative of hydroquinone, was commercialized but has been identified as having little whitening effect, and ascorbic acid, kojic acid, etc. have so poor product stability that they can only be restrictively used. While, extracts from licorice root, mori cortex radicis, etc. have been widely known to have a skin-whitening effect since ancient times. But, those extracts occasionally have poor effect according to the place of production it is difficult to keep the quality of the product constant(see, Fragrance J., 6, 59, 1990). Carzinol F extracted from a paper mulberry tree(see, Chem. Parm, Bull., 34(5), 1968, 1986; Cosmetics & Toiletries, 101, 51, 1995) was recently commercialized due to its good inhibitory activity against tyrosinase. However, this substance also has the problem that it is difficult to keep the quality of the product constant because carzinol F is an extract too. Sufficient data on stimulating property and stability of carzinol F are not available and it has a demerit that it cannot be easily synthesized because of the prenylcatechol group included therein.

DISCLOSURE OF INVENTION

Thus, the present inventors have intensively studied to develop a novel compound having an excellent inhibitory acitivity against tyrosinase in a small quantity. Further, the desired compound should be easily synthesized from the starting material and be stable. During the study, the present inventors analyzed the effect and structure of various natural substances known to have a whitening effect. As a result, we have developed a novel 1,3-diphenylpropane derivative of formula (I), which satisfies the purpose as mentioned above, and thus completed the present invention.

Therefore, it is an object of the present invention to provide a novel 1,3-dipenylpropane derivative represented by the following formula (I):

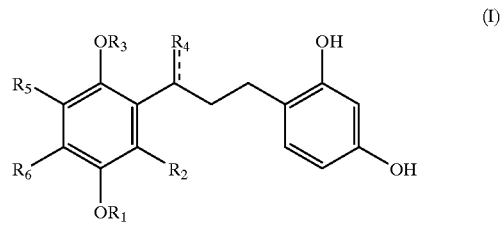

in which
- -- represents double or single bond,
- $R_1$ represents hydrogen or $C_1$–$C_{10}$ alkyl,
- $R_2$ represents $C_1$–$C_5$ alkyl or $C_1$–$C_5$ alkoxyalkyil, or
- $R_1$ and $R_2$ together represent a 5 to 6 membered heterocycle which can be substituted by $C_1$–$C_5$ alkyl and which contains oxygen as the hetero atom,
- $R_3$ represents hydrogen or $C_1$–$C_7$ alkyl,
- $R_4$ represents hydrogen, hydroxy, or oxo, and
- $R_5$ and $R_6$ independently of one another represent hydroge n or $C_1$–$C_5$ alkyl.

Among the foregoing definitions for the substituents of the compound of formula (I), the term "alkyl" defines straight or branched saturated hydrocarbon radicals such as methyl, ethyl, n-propyl, isopropyl or several butyl isomers when it is used alone or in the composite form such as "alkyloxy" or "alkoxyalkyl".

It is another object of the present invention to provide novel processes for preparing the compound of formula (I).

BEST MODE FOR CARRYING OUT THE INVENTION

Among the novel compound of formula (I), as defined above, the preferred compounds include those wherein $R_1$ represents hydrogen, methyl or ethyl, $R_2$ represents methyl, or $R_1$ and $R_2$ together represent,

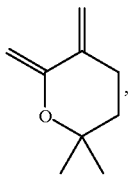

$R_3$ represents hydrogen or methyl, $R_4$ represents hydrogen or hydroxy, $R_5$ and $R_6$ independently of one another represent methyl.

Among the compound of formula (I), a compound represented by the following formula (Ia) wherein $R_4$ is hydroxy can be prepared conveniently by reducing a compound represented by the following formula (IV) in a solvent to a compound represented by the following formula (V) then by removing the protecting groups, as depicted in the following reaction scheme 1.

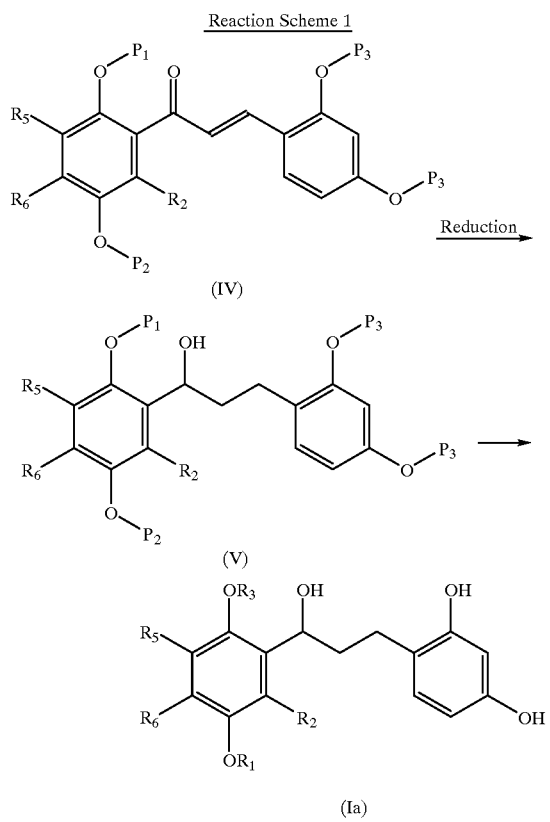

in which $P_1$, $P_2$ and $P_3$ are hydroxy protecting groups, that is $P_1$ represents benzyl, methyl, ethyl, tetrahydropyranyl, methoxymethyl, methoxyethoxymethyl or p-methoxybenzyl, $P_2$ represents benzyl, methyl or ethyl, $P_3$ represents benzyl, tetrahydropyranyl, methoxymethyl, methoxyethoxy methyl or p-methoxybenzyl, $R_1$ to $R_3$, $R_5$ and $R_6$ are defined as previously described.

The process described in the reaction scheme 1 above will be more specifically explained in the following.

In the reaction step for preparing the compound (V) by reducing the compound (IV), ethers such as diethylether, tetrahydrofuran(THF), etc. can be preferably used as the solvent and lithium aluminum hydride(LAH) can be preferably used as the reducing agent. It is desirable to carry out the reaction at temperatures ranging from −30 to 30° C. After the reduction is completed, protecting groups included in the compound (V) are eliminated to produce the compound (Ia). The protecting groups may be readily removed by conventionally known processes depending on the protecting groups to be removed. The selection of an appropriate deprotection condition can be made by a person having ordinary skill in this art. Particularly, when the protecting group is benzyl, the compound (Ia) can be prepared by carrying out a hydrogenation reaction in ethylacetate or by refluxing in a solvent mixture of hydrochloric acid and acetic acid.

Reduction of the compound (IV) to the compound (V) may be commonly carried out according to the aforementioned processes. However, the compound (V) can also be prepared by reducing in advance the double bond of the compound (IV) through a hydrogenation($H_2$, Pd-C) to obtain a ketone compound represented by the following formula (V') and then by converting the ketone group of the compound (V') to an alcohol group of the compound (V).

On the other hand, a compound represented by the following formula (Ib) wherein $R_4$ is oxo can be prepared by removing the protecting groups contained in the compound (V') instead of reducing the same. The compound (Ib) can also be reduced into the compound (Ia) in the presence of sodium borohydride or lithium aluminum hydride.

The processes as explained above are summarized in the reaction scheme 2 below.

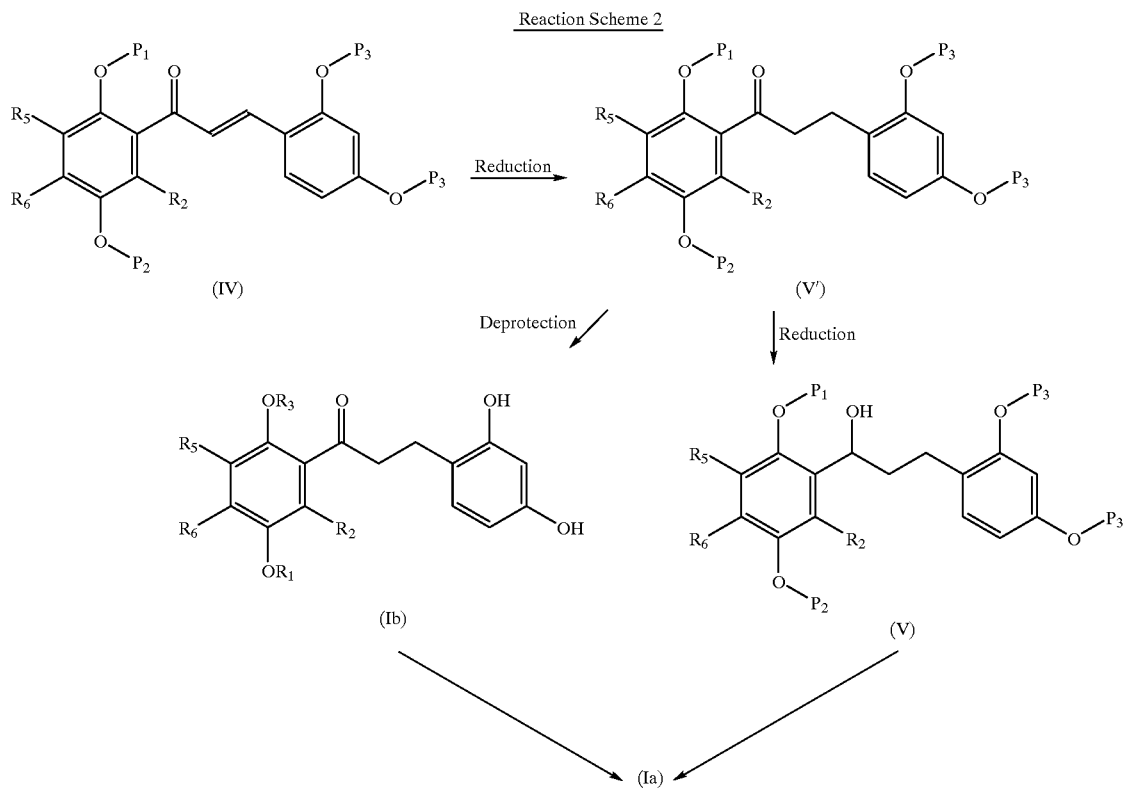

Reaction Scheme 2 in which

P$_1$, P$_2$, P$_3$, R$_1$ to R$_3$, R$_5$ and R$_6$ are defined as previously described.

In the above reaction scheme 2, the reduction from the compound (IV) to the compound (V') is achieved by hydrogenating the double bond contained in the compound (IV) for 2 hours under normal temperature and pressure in a solvent such as ethylacetate. The ketone compound (V') is reduced to the alcohol compound (V) through a treatment by sodium borohydride or lithium aluminum hydride. The process for obtaining the compound (Ib) by carrying out a deprotection on the compound (V') is identical to that explained for the reaction scheme 1 above. Particularly, when the protecting group is benzyl, the compound (Ib) can be prepared from the compound (V') by hydrogenating (i) in a solvent of ethylacetate for 10 to 15 hours under normal temperature and 2 to 4 atms, or (ii) in a solvent mixture of ethylacetate and a lower alcohol (methanol, ethanol, isopropanol, etc.) for 20 minutes to one hour under temperatures ranging from 35 to 55° C. and normal pressure, or it is also possible to obtain the compound (Ib) directly from the compound (IV) by the hydrogenation under the condition (i) or (ii).

The compound (IV) used as a starting material in the reaction scheme 1 can be prepared by condensing a compound of formula (II) with a compound of formula (III) in a solvent in the presence of a base, as depicted in the following reaction scheme 3.

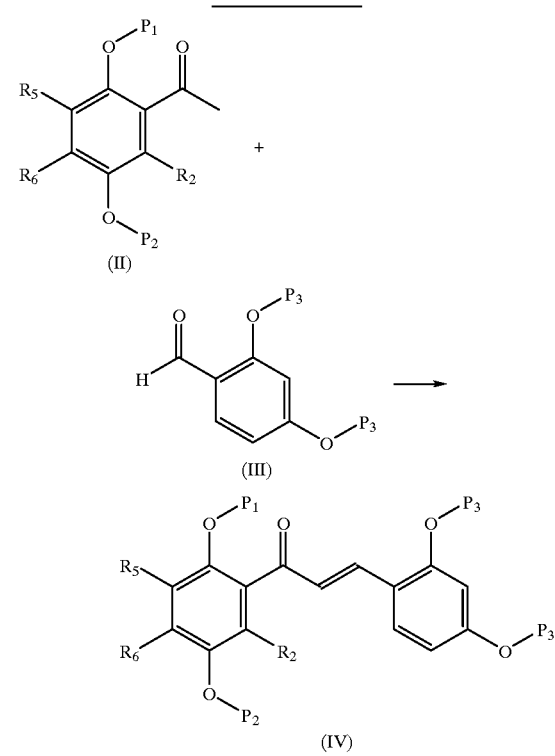

Reaction Scheme 3 in which $P_1$, $P_2$, $P_3$, $R_2$, $R_5$ and $R_6$ are defined as previously described.

In this reaction, it is preferable to use one or more selected from a group consisting of ethanol, tetrahydrofuran and dimethylformamide as the solvent, and to use one or more selected from a group consisting of sodium hydroxide, potassium hydroxide and sodium hydride as the base. The desired product is obtained by stirring the reactants for about 5 to 24 hours. When $P_1$ and $P_2$ are different from each other, the compound of formula (II) can readily be prepared from the existing compounds(see, Chem. Ber., 95, 1413, 1962; J. Med. Chem., 34, 2152, 1991).

Among the compounds of formula (Ia), the compound wherein $R_1$ and $R_2$ together form a heterocycle can be prepared according to the same procedure as explained above using a compound represented by the following formula (IIa)(see, J. Chem. Soc. Perkin Trans I, 1437, 1981) instead of the compound of formula (II).

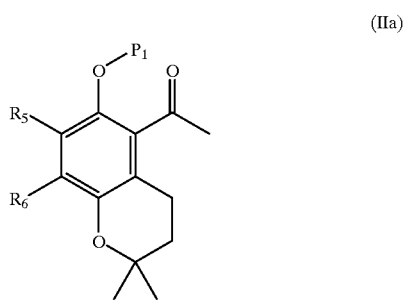

(IIa)

Finally, a compound represented by the following formula (Ic) wherein $R_4$ is hydrogen can be prepared, as depicted in the following reaction scheme 4, by dehydrating the compound (V) in a solvent in the presence of an acid to produce a compound represented by the following formula (VI) and then by reducing and deprotecting the compound (VI) thus produced.

Reaction Scheme 4

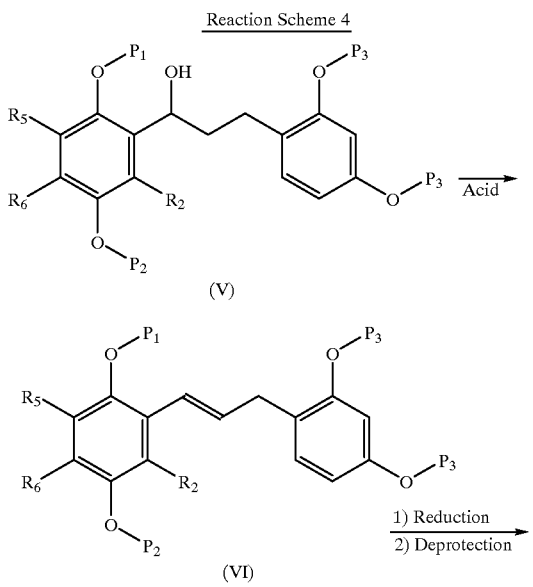

-continued

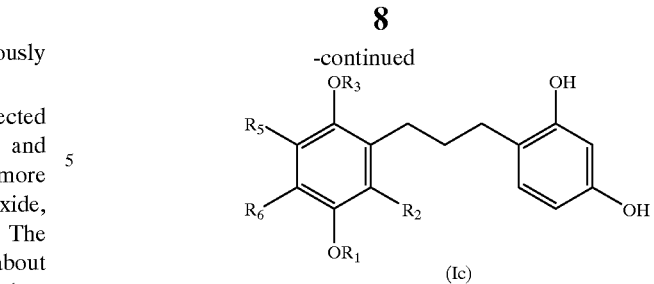

(Ic)

in which
$P_1$ to $P_3$, $R_1$ to $R_3$, $R_5$ and $R_6$ are defined as previously described.

The process described in reaction scheme 4 will be specifically explained below.

The compound (V) is dehydrated in one or more solvents selected from a group consisting of benzene, toluene and xylene in the presence of one or more acids selected from a group consisting of sulfuric acid, phosphoric acid and p-toluenesulfonic acid to produce the compound (VI). This dehydration reaction is preferably carried out at temperatures ranging from 80 to 100° C. The desired compound (Ic) is obtained by reducing the compound (VI) through a hydrogenation reaction and then by removing the protecting groups. Process for removing the protecting groups is carried out according to the same procedure as reaction scheme 1.

Typical examples of the compound (I) prepared according to the processes as explained above are represented in the following Table 1.

TABLE 1

| COM. NO. | $R_1$ | $R_2$ | $R_3$ | $R_4$ | $R_5$ | $R_6$ |
|---|---|---|---|---|---|---|
| 1 | —H | —Me | —H | —OH | —Me | —Me |
| 2 | —H | —Me | —H | —H | —Me | —Me |
| 3 | —H | —Me | —Me | —OH | —Me | —Me |
| 4 | —H | —Me | —Me | —H | —Me | —Me |
| 5 | —Me | —Me | —H | —OH | —Me | —Me |
| 6 | —Me | —Me | —H | —H | —Me | —Me |
| 7 | —Et | —Me | —H | —OH | —Me | —Me |
| 8 | (ring) | | —H | —OH | —Me | —Me |
| 9 | (ring) | | —H | —H | —Me | —Me |

Next, the present inventors have identified the inhibitory activity against tyrosinase of the compound (I) of the present invention according to the following procedure. That is, a sample is introduced into a microplate, to which are added a phosphate buffer solution(pH 6.8) and a L-tyrosine solution. Enzymatic reaction is started by the addition of a tyrosinase enzyme solution to the above mixture and then absorbance at 475 nm was measured to calculate the inhibition(%) against tyrosinase(see, Experimental Example 1).

In addition, in order to determine the inhibitory activity of the compound (I) againt melanin biosynthesis, this compound is added to a culture media comprising B-16 melanoma cells and incubated. Then, the cells are centrifuged to extract melanin and the amount of melanin produced is measured based on the absorbance(see, Experimental Example 2).

As a result, the compound of formula (I) according to the present invention is identified to have a superior or similar inhibitory effect against tyrosinase activity and melanin biosynthesis to that of the existing whitening substances. Therefore, it is possible to apply the compound of the present invention having such an effect to medicaments, non-medicinal supplies and cosmetics. The applying dosage of the compound (I) can be varied with the formulation type, purpose of use, etc.

The present invention will be more specifically explained by the following preparations, examples and experimental examples. However, it should be understood that the examples are intended to illustrate but not to in any manner limit the scope of the present invention.

PREPARATION 1

Synthesis of 3-(2,4-dibenzyloxy-phenyl)-1-(2,5-dibenzyloxy-3,4,6-trimithyl-phenyl)-propenone

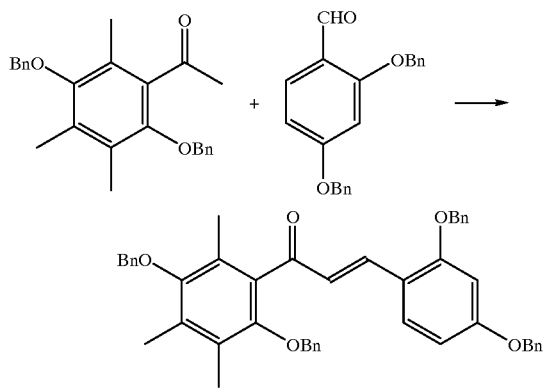

1.7 g(4.54 mmol) of 1-(2,5-dibenzyloxy-3,4,6-trimethyl-phenyl)-ethanone and 2.9 g(9.08 mmol) of 2,4-dibenzyloxy-benzaldehyde were dissolved in 32 ml of a solvent mixture of ethanol and tetrahydrofuran(1/1, v/v), to which was slowly added dropwise 6 ml of 50% aqueous sodium hydroxide solution. After the addition was completed, the reaction mixture was stirred for 16 hours at normal temperature. The solvent was removed by distillation under reduced pressure and the resulting residue was diluted with 25 ml of water, which was then neutralized to pH 7 with 10% aqueous HCl solution. This reaction solution was extracted with ethylacetate and then the solvent contained therein was removed by distillation under reduced pressure. The resulting mixture having a high viscosity was subjected to a silica gel column chromatography (eluent: n-hexane/ethylacetate= 7/1, v/v) to obtain 1.8 g(2.61 mmol, Yield 58%) of the title compound.

EXAMPLE 1

Synthesis of 4-[3-hydroxy-3-(2,5-dihydroxy-3,4,6-trimethyl-phenyl)-propyl]-benzene-1,3-diol Step 1: Preparation of 3-(2,4-dibenzyloxy-phenyl)-1-(2,5-dibenzyloxy-3,4,6-trimethyl-phenyl)-propan1-ol

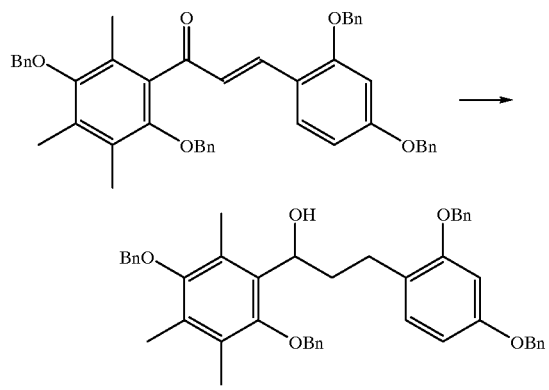

Method 1

0.57g(0.83 mmol) of 3-(2,4-dibenzyloxy-phenyl)-1-(2,5-dibenzyloxy-3,4,6-trimethyl-phenyl)-propenone prepared in Preparation 1 was dissolved in 5 ml of dry tetrahydrofuran and 0.1 g(2.52 mmol) of lithium aluminum hydride(LAH) was added thereto little by little while stirring at −30° C. The reaction solution was stirred for one hour, 0.1 ml of water, 0.1 ml of 15% aqueous NaOH solution and 0.3 ml of water were added to the solution in order and then the whole mixture was stirred for further 30 minutes. The resulting precipitate was filtered off and the filtrate was distilled to obtain a white solid, which was then purified by a silica gel column chromatography(eluent: n-hexane/ethylacetate=5/1, v/v) to obtain 0.56 g(Yield 98%) of the title compound.

Method 2

0.15g(0.22 mmol) of 3-(2,4-dibenzyloxy-phenyl)-1-(2,5-dibenzyloxy-3,4,6-trimethyl-phenyl)-propenone prepared in Preparation 1 was dissolved in 4 ml of ethylacetate(EtOAc). To this solution was slowly added 5 mg of 10% palladium-carbon catalyst, which was reacted for 30 minutes under pressurized hydrogen atmosphere(2 atm). The reaction solution was diluted with 50 mg of ethylacetate and then filtered. The filtrate was distilled under reduced pressure to produce 0.17 g of 3-(2,4-dibenzyloxy-phenyl)-1-(2,5-dibenzyloxy-3,4,6-trimethyl-phenyl)-propanone. 0.17 g(0.22 mmol) of the compound thus produced was dissolved in 2 ml of methanol, 20 mg(0.53 mmol) of sodium boro hydride(NaBH$_4$) was added thereto little by little at 0° C. The mixture was stirred for 10 minutes at 0° C. and then the solvent was eliminated by distillation under reduced pressure . The residue was diluted with 10 ml of water, extracted with ethylacetate and dried over anhydrous sodium sulfate. The solvent was distilled under reduced pressure and the residue was subjected to a silica gel column chromatography(eluent: n-hexane/ethylacetate=1/1, v/v) to obtain 0.1 g(Yield 66%) of the title compound.

Step 2: Preparation of 4-[3-hydroxy-3-(2,5-dihydroxy-3,4, 6-trimethyl-phenyl)-propyl]-benzene-1,3-diol

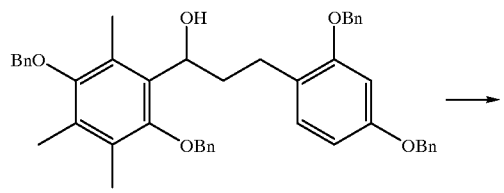

-continued

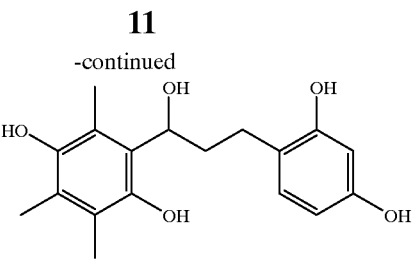

0.31 g(0.45 mmol) of 3-(2,4-dibenzyloxy-phenyl)-1-(2,5-dibenzyloxy-3,4,6-trimethyl-phenyl)-propan-1-ol was dissolved in 6 ml of ethylacetate. To this solution was slowly added 10 mg of 10% palladium-carbon catalyst, which was reacted for 12.5 hours under pressurized hydrogen atmosphere(4 atm). The reaction solution was diluted with 50 ml of ethylacetate and then filtered. The filtrate was distilled under reduced pressure to obtain 0.14 g (Yield 100%) of the title compound.

EXAMPLE 2

Synthesis of 4-13-(2,5-dihydroxy-3,4,6-trimethyl-phenyl)-propyll-benzene-1,3-diol

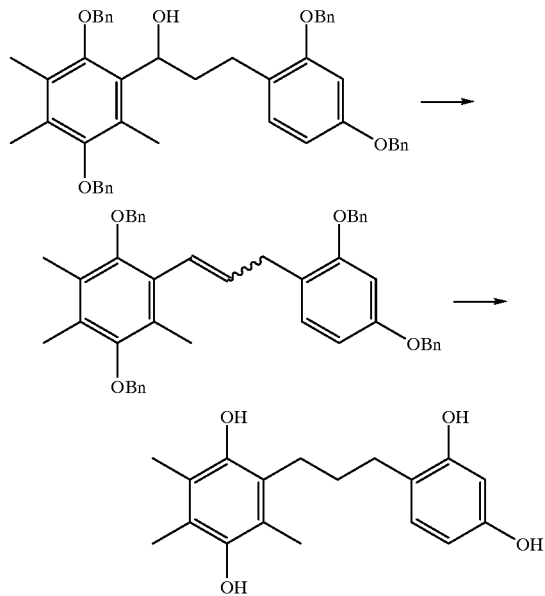

2.39 g(3.46 mmol) of 3-(2,4-dibenzyloxy-phenyl)-1-(2,5-dibenzyloxy-3,4,6-trimethyl-phenyl)-propan-1-ol was diluted with 100 ml of dry benzene and 30 mg of p-toluenesulfonic acid was added thereto. The mixture was stirred for 4 hours while refluxing to eliminate water. The solution thus produced was cooled down to room temperature and washed once(×1) with saturated aqueous sodium hydrogen carbonate solution. The washings was extracted with dichloromethane and the extract was combined with the original organic layer. Then, the combined mixture was dried, distilled under reduced pressure and subjected to a silica gel column chromatography(eluent: n-hexane/ethylacetate=10/1, v/v) to obtain 2.1 g(Yield 90%) of 4-[3-(2,5-dibenzyloxy-3,4,6-trimethylphenyl)-allyl]-1,3-dibenzyloxy-benzene. 2.1 g(3.12 mmol) of the compound thus obtained was diluted with 30 ml of ethylacetate, to which was slowly added 45 mg of 10% palladium catalyst. The resulting solution was stirred for 72 hours under hydrogen atmosphere of 60 psi, diluted with 50 ml of ethylacetate and then filtered. The filtrate was distilled under reduced pressure and subjected to a silical gel column chromatography(eluent: n-hexane/ethylacetate=1/1, v/v) to obtain 0.74 g (Yield 79%) of the title compound.

PREPARATION 2

Synthesis of 3-(2,4-dibenzyloxy-phenyl)-1-(5-benzyloxy-2-methoxy-3,4,6-trimethyl-phenyl)-propenone

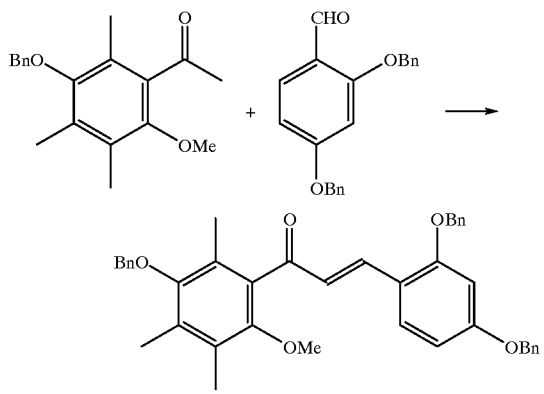

0.23 g(0.77 mmol) of 1-(5-benzyloxy-2-methoxy-3,4,6-trimethyl-phenyl)-ethanone and 0.62 g(1.94 mmol) of 2,4-dibenzyloxybenzaldehyde were dissolved in 7 ml of a solvent mixture of ethanol and tetrahydrofuran(1/1, v/v) and then 1.5 ml of 50% aqueous sodium hydroxide solution was slowly added dropwise thereto. After the addition was completed, the mixture was stirred for 16 hours at normal temperature. The solvent contained therein was removed, the residue was diluted with water and neutralized to pH 7 using 10% aqueous hydrochloric acid solution. This solution was extracted with ethylacetate and the solvent was removed by distillation under reduced pressure. The residue having a high viscosity was subjected to a silica gel column chromatography (eluent: n-hexane/ethylacetate=7/1, v/v) to obtain 0.30 g(Yield 65%) of the title compound.

EXAMPLE 3

Synthesis of 4-[3-hydroxy-3-(5-hydroxy-2-methoxy-3,4,6-trimethyl-phenyl)-propyl]-benzene-1,3-diol

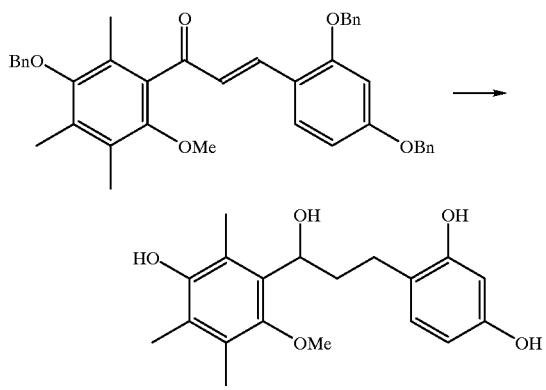

290 mg(0.48 mmol) of 3-(2,4-dibenzyloxy-phenyl)-1-(5-benzyloxy-2-methoxy-3,4,6-trimethyl-phenyl)-propenone prepared in Preparation 2 was dissolved in 5 ml of ethylacetate. To this solution was slowly added 15 mg of 10% palladium-carbon catalyst, which was reacted for 12 hours under pressurized hydrogen atmosphere(4 atm). The reaction solution was diluted with 100 ml of ethylacetate and then filtered. The filtrate was distilled under reduced pressure to obtain 160 mg(0.48 mmol, Yield 98%) of 3-(2,4-dihydroxy-phenyl)-1-(5-hydroxy-2-methoxy-3,4,6-trimethyl-phenyl)-propanone. 160 mg(0.48 mmol) of the compound thus obtained was dissolved in 2 mg of diethylether and 160 mg (4.21 mmol) of lithium aluminum hydride was added thereto little by little at 0° C. After stirring for one hour, 0.1 ml of water, 0.1 ml of 15% aqueous NaOH solution and 0.3 ml of water were added thereto in order and the mixture was stirred for further 30 minutes. The resulting precipitate was filtered off and the filtrate was distilled to obtain a white solid which was then subjected to a silical gel column chromatography(eluent: n-hexane/ethylacetate=5/1, v/v) to obtain 158 mg(Yield 98%) of the title compound.

EXAMPLE 4

Synthesis of 4-[3-(2-methoxy-5-hydroxy-3,4,6-trimethyl-phenyl)-propyll-benzene-1,3-diol

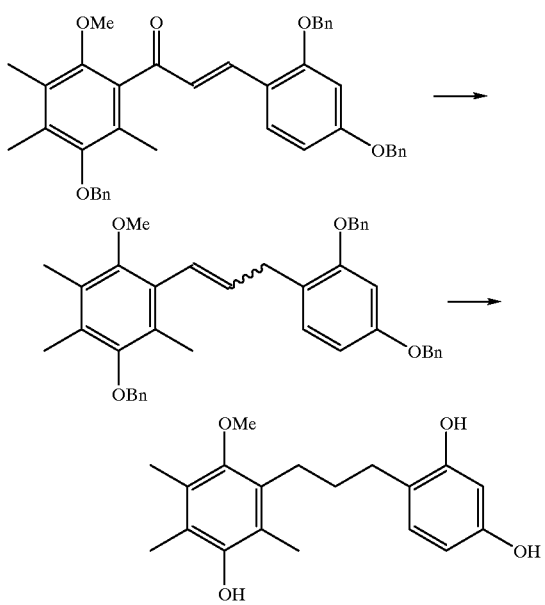

550 mg(0.92 mmol) of 3-(2,4-dibenzyloxy-phenyl)-1-(5-benzyloxy-2-methoxy-3,4,6-trimethyl-phenyl)-propenone was dissolved in 7 ml of ethylacetate. To this solution was slowly added 15 mg of 10% palladium-carbon catalyst, and reacted for 2 hours under hydrogen atmosphere of normal pressure(1 atm). The reaction solution was diluted with 15 ml of ethylacetate and then filtered. The filtrate was distilled under reduced pressure to obtain 552 mg(Yield 100%) of 3-(2,4-dibenzyloxy-phenyl)-1-(2-methoxy-5-benzyloxy-3,4,6-trimethyl-phenyl)-propanone. 225 mg(0.37 mmol) of the compound thus obtained was reduced by $NaBH_4$ to an alcohol compound which was then diluted with 10 ml of dry benzene. 30 mg of p-toluenesulfonic acid was added thereto and the mixture was stirred for 4 hours while refluxing. The reaction solution was cooled down to room temperature and then washed with saturated aqueous sodium hydrogen carbonate solution once(×1). The washings was extracted again with dichloromethane and the extract was combined with the original organic layer. Then, the combined mixture was dried, distilled under reduced pressure and subjected to a silica gel column chromatography(eluent: n-hexane/ethylacetate=10/1, v/v) to obtain 169 mg(0.29 mmol, Yield 78%) of 4-[3-(2-methoxy-5-benzyloxy-3,4,6-trimethyl-phenyl)-allyl]-1,3-dibenzyloxy-benzene. 160 mg(0.27 mmol) of the compound thus obtained was diluted with 30 ml of ethylacetate, to which was slowly added 45 mg of 10% palladium catalyst. The resulting mixture was stirred for 48 hours under hydrogen atmosphere of 60 psi, diluted with 10 ml of ethylacetate and then filtered. The filtrate was distilled under reduced pressure and the residue was subjected to a silica gel column chromatography(eluent: n-hexane/ethylacetate=1/1, v/v) to obtain 74 mg(0.234 mmol, Yield 86%) of the title compound.

PREPARATION 3

Synthesis of 3-(2,4-dibenzyioxy-phenyl)-1-(2-benzyloxy-5-methoxy-3,4,6-trimethyl-phenyl)-propenone

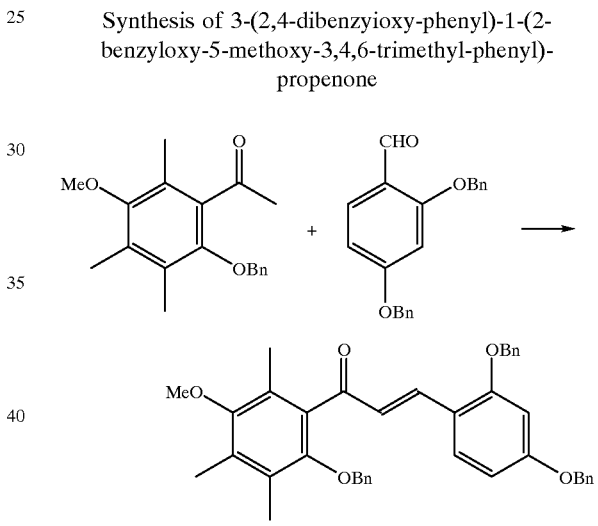

1.22 g(4.09 mmol) of 1-(2-benzyloxy-5-methoxy-3,4,6-trimethyl-phenyl)-ethanone and 2.8 g(9 mmol) of 2,4-dibenzyloxy-benzaldehyde were dissolved in 40 ml of a solvent mixture of ethanol and tetrahydrofuran(1/1, v/v), to which was slowly added dropwise 10 mg of 50% aqueous sodium hydroxide solution. After the addition was completed, the mixture was stirred for 16 hours at normal temperature. The solvent contained in the reaction solution was removed by distillation under reduced pressure, the resulting residue was diluted with 40 ml of water and then neutralized to pH 7 using 10% aqueous hydrochloric acid solution. This solution was extracted with ethylacetate and the solvent contained in the extract was removed by distillation under reduced pressure. The resulting mixture having a high viscosity was subjected to a silica gel column chromatography(eluent: n-hexane/ethylacetate=7/1, v/v) to obtain 2.37 g(Yield 97%) of the title compound.

EXAMPLE 5

Synthesis of 4-[3-hydroxy-3-(2-hydroxy-5-methoxy-3,4,6-trimethyl-phenyl)-propyl]-benzene-1,3-diol

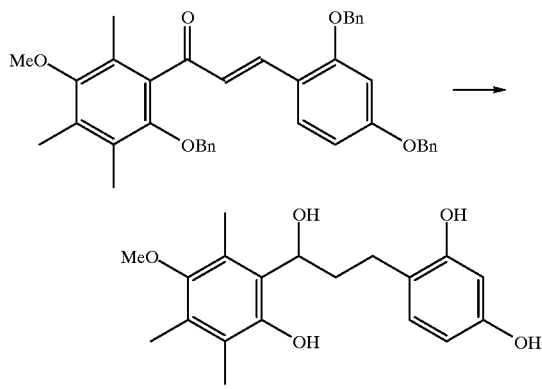

1.28 g(0.21 mmol) of 3-(2,4-dibenzyloxy-phenyl)-1-(2-benzyloxy-5-methoxy-3,4,6-trimethyl-phenyl)-propenone prepared in Preparation 3 was dissolved in 6 ml of ethylacetate. To this solution was slowly added 45 mg of 10% palladium-carbon catalyst, which was reacted for 12 hours under pressurized hydrogen atmosphere(4 atm). The reaction solution was diluted with 50 ml of ethylacetate and then filtered. The filtrate was distilled under reduced pressure to obtain 660 mg(Yield 95%) of 3-(2,4-dihydroxy-phenyl)-1-(2-hydroxy-5-methoxy-3,4,6-trimethyl-phenyl)-propanone. 660 mg(2 mmol) of the compound thus obtained was dissolved in 12 ml of diethylether, 750 mg of lithium aluminum hydride was added thereto little by little at 0° C. and then the mixture was stirred for one hour. After 1 ml of water, 1 ml of 15% aqueous NaOH solution and 3 ml of water were added to the reaction solution in order, the resulting solution was stirred for further 30 minutes. The precipitate produced was filtered off and the filtrate was distilled to obtain a white solid which was then subjected to a silica gel column chromatography(eluent: n-hexane/ethylacetate=5/1, v/v) to obtain 524 mg(1.58 mmol, Yield 79%) of the title compound.

EXAMPLE 6

Synthesis of 4-[3-(2-hydroxy-5-methoxy-3,4,6-trimethyl-phenyl)-propyl]-benzene-1,3-diol

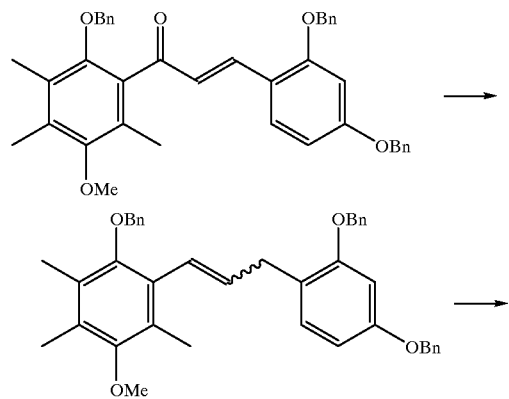

-continued

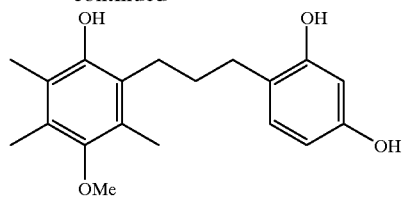

300 mg(0.50 mmol) of 3-(2,4-dibenzyloxy-phenyl)-1-(2-benzyloxy-5-methoxy-3,4,6-trimethyl-phenyl)-propenone was dissolved in 3 ml of ethylacetate. To this solution was slowly added 15 mg of 10% palladium-carbon catalyst, which was reacted for 3 hours under hydrogen atmosphere of normal pressure (1 atm). The reaction solution was diluted with 20 ml of ethylacetate and then filtered. The filtrate was distilled under reduced pressure to obtain 3-(2,4-dibenzyloxy-phenyl)-1-(2-benzyloxy-5-methoxy-3,4,6-trimethyl-phenyl)-propanone. The compound thus obtained was not further purified and reduced by 40 mg of NaBH$_4$ in 5 ml of methanol to an alcohol compound. The reaction solution containing the alcohol compound was distilled under reduced pressure to remove methanol and extracted with dichloromethane to obtain 277 mg(Yield 92%) of the alcohol compound, which was then diluted with 10 ml of dry benzene. 30 mg of p-toluenesulfonic acid was added thereto and the mixture was stirred for 4 hours while refluxing. The reaction solution was cooled down to room temperature and then washed with saturated aqueous sodium hydrogen carbonate solution once(×1). The washings was extracted again with dichloromethane and the extract was combined with the original organic layer. Then, the combined mixture was dried, distilled under reduced pressure and subjected to a silica gel column chromatography(eluent: n-hexane/ethylacetate=10/1, v/v) to obtain 244 mg(0.42 mmol, Yield 91%) of 4-[3-(2-benzyloxy-5-methoxy-3,4,6-trimethyl-phenyl)-allyl]-1,3-dibenzyloxy-benzene. The compound thus obtained was diluted with 30 ml of ethylacetate, to which was slowly added 45 mg of 10% palladium catalyst. The resulting mixture was stirred for 20 hours under hydrogen atmosphere of 60 psi, diluted with 10 ml of ethylacetate and then filtered. The filtrate was distilled under reduced pressure and the residue was subjected to a silica gel column chromatography (eluent: n-hexane/ethylacetate=1/1, v/v) to obtain 118 mg(Yield 88%) of the title compound.

PREPARATION 4

Synthesis of 3-(2,4-dibenzyloxy-phenyl)-1-(2-benzyloxy-5-ethoxy-3,4,6-trimethyl-phenyl)-propenone

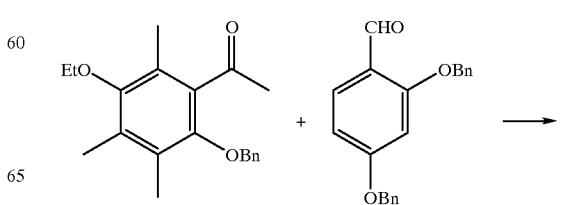

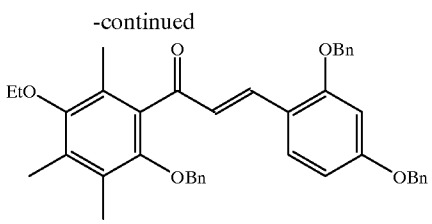

310 mg(1 mmol) of 1-(2-benzyloxy-5-ethoxy-3,4,6-trimethyl-phenyl)-ethanone and 650 mg(2.1 mmol) of 2,4-dibenzyloxy-benzaldehyde were dissolved in 15 ml of a solvent mixture of ethanol and tetrahydrofuran(1/1, v/v), to which was slowly added dropwise 5 mg of 50% aqueous sodium hydroxide solution. After the addition was completed, the mixture was stirred for 24 hours at normal temperature. The solvent contained in the reaction solution was removed by distillation under reduced pressure, the resulting residue was diluted with 10 ml of water and then neutralized to pH 7 using 10% aqueous hydrochloric acid solution. This solution was extracted with ethylacetate and the solvent contained in the extract was removed by distillation under reduced pressure. The residue was subjected to a silica gel column chromatography (eluent: n-hexane/ethylacetate=7/1, v/v) to obtain 440 mg(Yield 72%) of the title compound.

EXAMPLE 7

Synthesis of 4-13-hydroxy-3-(2-hydroxy-5-ethoxy-3,4,6-trimethyl-phenyl)-propyl]-benzene-1,3-diol

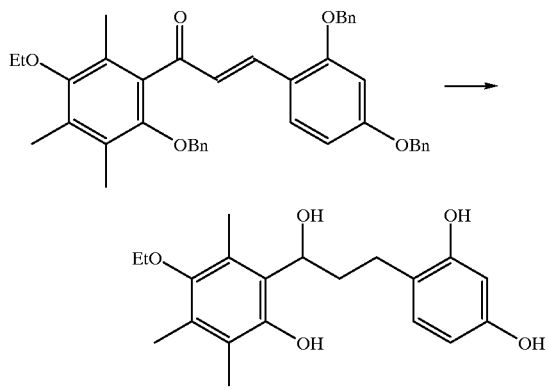

440 mg(0.72 mmol) of 3-(2,4-dibenzyloxy-phenyl)-1-(2-benzyloxy-5-ethoxy-3,4,6-trimethyl-phenyl)-propenone prepared in Preparation 4 was dissolved in 6 ml of ethylacetate. To this solution was slowly added 15 mg of 10% palladium-carbon catalyst, which was then reacted for 15 hours under pressurized hydrogen atmosphere(4 atm). The reaction solution was diluted with 30 ml of ethylacetate and then filtered. The filtrate was distilled under reduced pressure to obtain 205 mg(Yield 91%) of 3-(2,4-dihydroxyphenyl)-1-(2-hydroxy-5-ethoxy-3,4,6-trimethyl-phenyl)-propanone. 205 mg(0.66 mmol) of the compound thus obtained was dissolved in 12 ml of diethylether, 200 mg of lithium aluminum hydride was added thereto little by little at 0° C. and then the mixture was stirred for one hour. After 0.2 ml of water, 0.2 ml of 15% aqueous NaOH solution and 0.6 ml of water were added to the reaction solution in order, the resulting solution was stirred for further 30 minutes. The precipitate produced was filtered off and the filtrate was distilled to obtain a white solid, which was then subjected to a silica gel column chromatography(eluent: n-hexane/ethylacetate=5/1, v/v) to obtain 160 mg(Yield 70%) of the title compound.

PREPARATION 5

Synthesis of 3-(2,4-dibenzyloxy-phenyl)-1-(6-benzyloxy-2,2,7,8-tetramethyl-chroman-5-yl)-propenone

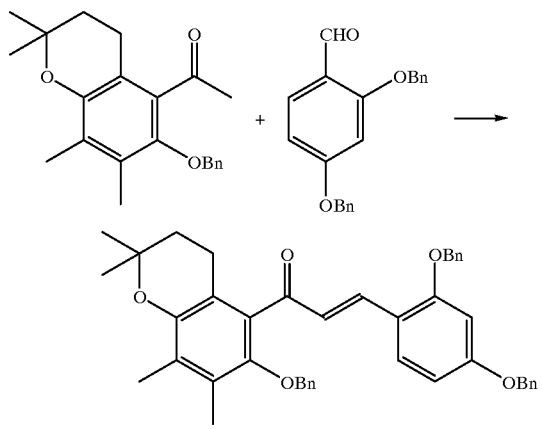

1.69 g(5 mmol) of 1-(6-benzyloxy-2,2,7,8-tetramethyl-chroman-5-yl)-ethanone and 3.2 g(10.5 mmol) of 2,4-dibenzyloxy-benzaldehyde were dissolved in 50 ml of a solvent mixture of ethanol and tetrahydrofuran(1/1, v/v), to which was slowly added dropwise 10 ml of 50% aqueous sodium hydroxide solution. After the addition was completed, the mixture was stirred for 16 hours at normal temperature. After the solvent contained in the reaction solution was removed by distillation under reduced pressure, the residue was diluted with 50 ml of water and then neutralized to pH 7 using 10% aqueous hydrochloric acid solution. This solution was extracted with ethylacetate and the solvent contained in the extract was removed by distillation under reduced pressure. The residue was subjected to a silica gel column chromatography(eluent: n-hexane/ethylacetate=7/1, v/v) to obtain 2.13 g(Yield 68%) of the title compound.

EXAMPLE 8

Synthesis of 4-[3-hydroxy-3-(6-hydroxy-2,2,7,8-tetramethyl-chroman-5-yl)-propyl]-benzene-1,3-diol

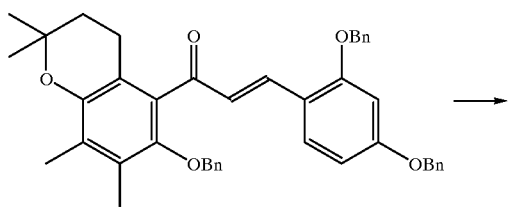

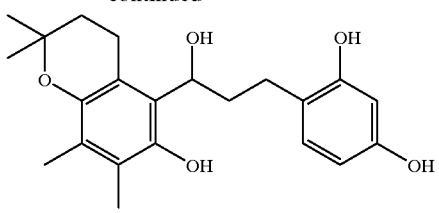

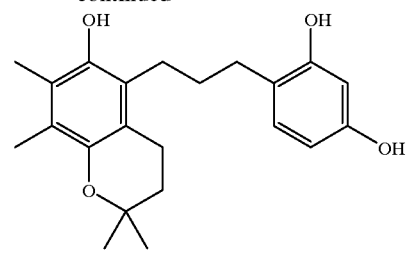

2.13 g(3.33 mmol) of 3-(2,4-dibenzyloxy-phenyl)-1-(6-benzyloxy-2,2,7,8-tetramethyl-chroman-5-yl)-propenone prepared in Preparation 5 was dissolved in 5 ml of ethylacetate. To this solution was slowly added 30 mg of 10% palladium-carbon catalyst, which was then reacted for 12 hours under pressurized hydrogen atmosphere(4 atm). The reaction solution was diluted with 50 ml of ethylacetate and then filtered. The filtrate was distilled under reduced pressure to obtain 1.14 g(0.31 mmol, Yield 94%) of 3-(2,4-dihydroxyphenyl)-1-(6-hydroxy-2,2,7,8-tetramethyl-chroman-5-yl)-propanone. 1.14 g of the compound thus obtained was dissolved in 10 ml of diethylether, 1.0 g of lithium aluminum hydride was added thereto little by little at 0° C. and then the mixture was stirred for one hour. After 1 ml of water, 1 ml of 15% aqueous NaOH solution and 3 ml of water were added to the reaction solution in order, the resulting solution was stirred for further 30 minutes. The precipitate produced was filtered off and the filtrate was distilled to obtain a white solid, which was then subjected to a silica gel column chromatography(eluent: n-hexane/ethylacetate=1/1, v/v) to obtain 1.04 g(2.80 mmol, Yield 90%) of the title compound.

EXAMPLE 9

Synthesis of 4-[3-(6-hydroxy-2,2,7,8-tetramethyl-chroman-5-yl)-propyl]-benzene-1,3-diol

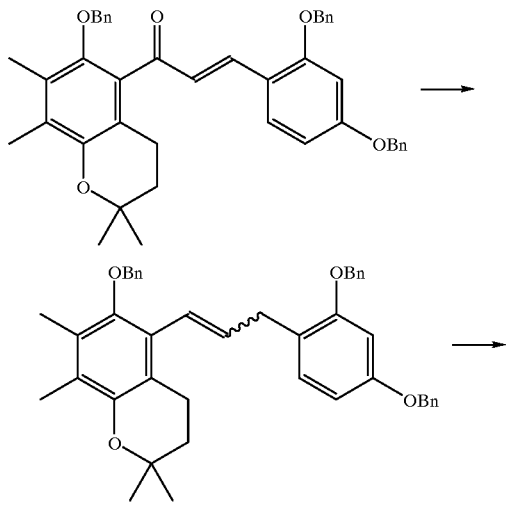

550 mg(0.86 mmol) of 3-(2,4-dibenzyloxy-phenyl)-1-(6-benzyloxy-2,2,7,8-tetramethyl-chroman-5-yl)-propenone prepared in Preparation 5 was dissolved in 7 ml of ethylacetate. To this solution was slowly added 1 mg of 10% palladium-carbon catalyst, which was then reacted for 2 hours under hydrogen atmosphere of normal pressure(1 atm). The reaction solution was diluted with 50 ml of ethylacetate and then filtered. The filtrate was distilled under reduced pressure to obtain 478 mg(0.75 mmol, Yield 87%) of 3-(2,4-dibenzyloxy-phenyl)-1-(6-benzyloxy-2,2,7,8-tetramethyl-chroman-5-yl)-propanone. 200 mg(0.31 mmol) of the compound thus obtained was reduced by 125 mg of $NaBH_4$ to an alcohol compound, which was then diluted with 10 ml of dry benzene. 30 mg of p-toluenesulfonic acid was added thereto and the mixture was stirred for 4 hours while refluxing. The reaction solution was cooled down to room temperature and then washed with saturated aqueous sodium hydrogen carbonate solution once(×1). The washings was extracted again with dichloromethane and the extract was combined with the original organic layer. Then, the combined mixture was dried, distilled under reduced pressure and subjected to a silica gel column chromatography(eluent: n-hexane/ethylacetate=10/1, v/v) to obtain 169 mg(0.271 mmol, Yield 88%) of an olefin compound. 160 mg (0.26 mmol) of this olefin compound thus obtained was diluted with 30 ml, of ethylacetate, to which was slowly added 4.5 mg of 10% palladium catalyst. The resulting mixture was stirred for 48 hours under hydrogen atmosphere of 60 psi, diluted with 10 ml of ethylacetate and then filtered. The filtrate was distilled under reduced pressure and the residue was subjected to a silica gel column chromatography(eluent: n-hexane/ethylacetate=3/1, v/v) to obtain 74 mg (0.21 mmol, Yield 80%) of the title compound.

EXAMPLE 10

Synthesis of 4-[3-hydroxy-3-(2-hydroxy-5-methoxy-3,4,6-trimethyl-phenyl)-propyl]-benzene-1,3-diol

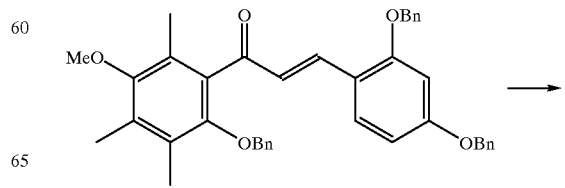

-continued

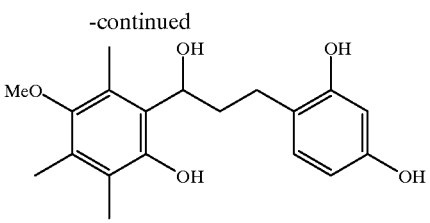

5.5 g(9.2 mmol) of 3-(2,4-dibenzyloxy-phenyl)-1-(2-benzyloxy-5-methoxy-3,4,6-trimethyl-phenyl)-propenone prepared in Preparation 3 was dissolved in 20 ml of a solvent mixture of ethanol and ethylacetate(1/3, v/v), to which was slowly added 50 mg of 10% palladium-carbon catalyst. The temperature of the mixture was raised to 40° C. and then hydrogenation was carried out for 0.5 hours at normal pressure. The reaction solution was diluted with 60 ml of ethylacetate, filtered and then the filtrate was distilled under reduced pressure.

The residue was diluted with diethylether, washed with aqueous sodium hydrogen carbonate solution, dried over anhydrous sodium sulfate and then filtered. The filtrate was distilled under reduced pressure to obtain 2.88 g(8.73 mmol, Yield 95%) of 3-(2,4-dihydroxy-phenyl)-1-(2-hydroxy-5-methoxy-3,4,6-trimethyl-phenyl)-propanone. 2.88 g(8.73 mmol) of the compound thus obtained was dissolved in 12 ml of methanol and 165 mg(4.37 mmol) of sodium borohydride was added thereto at 0° C. little by little. The reaction solution was stirred for one hour at normal temperature, distilled under reduced pressure, diluted with 10 ml of ethylacetate and then washed with 10 ml of water three times(×3). The organic layer separated was dried over anhydrous sodium sulfate and then filtered. The filtrate was distilled under reduced pressure and the residue was subjected to silica gel column chromatography (eluent: n-hexane/ethylacetate=5/1, v/v) to obtain 767 mg(2.31 mmol, Yield 80%) of the title compound.

The compounds represented in Table 1 were synthesized according to the Preparations and Examples above, and their physico-chemical properties are represented in the following Table 2.

TABLE 2

| COM. NO. | $^1$H NMR ppm(solvent) | (m.p.) ° C. |
|---|---|---|
| 1 | 6.90(d,1H), 6.35(d,1H), 6.25(dd,1H), 5.06(dd,1H), 2.72~2.82(m,1H), 2.55~2.70(m,1H), 2.10(s,3H), 2.04 (s,3H), 1.94(s,3H), 1.82~1.94(m,2H) (acetone d-6) | 202 |
| 2 | 6.87(d,1H), 6.37(d,1H), 6.25(dd,1H), 2.58(t,2H), 2.51(t,2H), 2.06(s,3H), 2.04(s,3H), 1.95(s,3H), 1.69(m,2H) (acetone d-6) | 194 |
| 3 | 6.86(d,1H), 6.26(d,1H), 6.20(dd,2H), 5.12(dd,1H), 3.56(s,3H), 2.60~2.72(m,1H), 2.42~2.55(m,1H), 2.25(s,3H), 2.15(s,3H), 2.13(s,3H), 1.80~1.95(m,2H) (CDCl$_3$) | 63 |
| 4 | 6.89(d,1H), 6.20~6.26(m,2H), 3.53(s,3H), 2.60(t,2H), 2.53(t,2H), 2.28(s,3H), 2.20(s,3H), 2.17(s,3H), 1.70~1.80(m,2H) (CDCl$_3$) | 58 |
| 5 | 6.93(d,1H), 6.40(d,1H), 6.29(dd,1H), 5.07(dd,1H), 3.51(s,3H), 2.85(m,1H), 2.68(m,1H), 2.10(s,3H), 2.06(m,1H), 1.95(s,3H), 1.85(m,1H) (acetone-d$_6$) | 202 |
| 6 | 6.88(d,1H), 6.38(d,1H), 6.25(dd,1H), 3.54(s,3H), 2.60~2.80(m,4H), 2.12(s,9H), 1.75~1.95(m,2H) (acetone-d$_6$) | 153 |
| 7 | 6.96(d,1H), 6.39(d,1H), 6.28(dd,1H), 5.08(dd,1H), 3.65(q,2H), 2.69~2.75(m,1H), 2.78~2.85(m,1H), | 132 |

TABLE 2-continued

| COM. NO. | $^1$H NMR ppm(solvent) | (m.p.) ° C. |
|---|---|---|
|  | 2.10(s,3H), 2.06(s,3H), 2.00(s,3H), 1.80~1.95(m,2H), 1.31(t,3H) (acetone-d-6) |  |
| 8 | 7.00(d,1H), 6.36(d,1H), 6.27(m,1H), 5.10(dd,1H), 2.72~2.82(1H,m), 2.56~2.70(m,3H), 2.14(s,3H), 2.12(s,3H), 1.70~1.95(m,4H), 1.36(s,3H), 1.28(s,3H) (CDCl$_3$) | 156 |
| 9 | 6.97(d,1H), 6.31~6.36(m,2H), 5.10~5.20(br,s,1H), 4.80~4.90(br,s,1H), 2.55~2.65(m,6H), 2.13(s,3H), 2.09(s,3H), 1.65~1.85(m,4H), 1.28(s,6H) (CDCl$_3$) | 134 |

The inhibitory effects against tyrosinase and melanin biosynthesis of the compound (I) of the present invention was measured according to the procedures described in the following Experimental Examples 1 and 2.

Experimental Example 1
Inhibitory Activity Against Tyrosinase

Enzyme tyrosinase extracted from mushrooms (manufactured by Sigma) was used in the present experiment. First, a substrate L-tyrosine was dissolved in phosphate buffer solution(0.05M, pH 6.8) to a concentration of 1.5 mM and then 0.01 ml of this solution was introduced to a 0.3 ml cuvette in a spectrophotometry. Dopa as a cofacter was prepared as a solution in a concentration of 0.06 mM and 0.01 ml of this dopa solution was added to the substrate solution. To the resulting mixture were added the inhibitor of formula (I) and phosphate buffer solution to a total volume of 0.31 ml. The reaction was started by adding 0.1 ml of an enzyme solution in which tyrosinase was dissolved in phosphate buffer solution in a concentration of 60 U/ml. 0.1 ml of phosphate buffer solution instead of the enzyme solution was added to the blank sample. The reaction was carried out for 10 minutes at 37° C. and then absorbance at 475 nm was measured using Spectrophotometer (Beckman DU-7500).

Inhibition(%) against tyrosinase of the compound (I) is calculated based on the absorbance at 475 nm and IC$_{50}$ value is determined as the concentration of the inhibitor when the inhibition(%) against enzyme activity reaches 50%. The Inibition(%) can be calculated according to the following formula and the results are represented in the following Table 3.

$$\text{Inhibition}(\%) = \frac{(A - B)}{A} \times 100$$

in the above formula

A represents absorbance at 475 nm when the inhibitor is added, and

B represents absorbance at 475 nm when the inhibitor is not added.

TABLE 3

| Inhibitory activity against tyrosinase | |
|---|---|
| Compound No. | IC$_{50}$(μg/ml) |
| 1 | 0.5 |
| 2 | 1 |
| 3 | 50 |
| 4 | 20 |
| 5 | 0.1 |
| 6 | 0.1 |

TABLE 3-continued

Inhibitory activity against tyrosinase

| Compound No. | IC$_{50}$(μg/ml) |
|---|---|
| 7 | 1.0 |
| 8 | 0.3 |
| 9 | 0.3 |
| Arbutin | 113 |
| Kojic acid | 3.1 |
| Hydroquinone | 0.5 |

As can be seen from the results in Table 3 above, the compound of formula (I) according to the present invention shows a similar or superior inhibitory activity against tyrosinase to the existing inhibitors. Thus, the present compounds can be used advantageously for such a purpose.

Experiment 2
Inhibitory Effect Against Melanin Biosynthesis in B-16 Mouse Melanoma Cell The compound according to the present invention was added to a culture media of B-16 mouse melanoma cell and observed in order to examine its whitening effect in cellular level.

B-16 mouse melanoma cells were cultured to a density of 10$^6$ cells/dish in culture media compounds in various concentrations were respectively added thereto and then cultured for 3 days. The cells were separated from the culture dish by the treatment with trypsin and then centrifuged to extract melanin(wherein a pellet was extracted using 2N perchloric acid). 1 ml of 1N aqueous sodium hydroxide solution was added to the melanin extracted and the resulting mixture was heated to dissolve melanrin. The absorbance at 400 nm was measured by a spectrophotometer and the amount of the melanin produced was represented by the absorbance per unit cell numbers(10$^6$ cell). IC$_{50}$ value is determined as the concentration of the inhibitor when the inhibition(%) against enzyme activity reaches 50% and the results are represented in the following Table 4.

TABLE 4

| Compound No. | IC$_{50}$(μg/ml) |
|---|---|
| 1 | 10 |
| 2 | 5 |
| 3 | 40 |
| 4 | 45 |
| 5 | 5 |
| 6 | 10 |
| 7 | 20 |
| 8 | 2 |
| 9 | 3 |
| Arbutin | 300 |
| Kojic acid | 15 |

The results of Table 4 shows that the compound according to the present invention exhibits an excellent inhibitory activity against melanin biosynthesis in mouse melanoma cell. Therefore, it is recognized that the compound of the present invention exhibits a distinguished whitening effect through the prevention of melanin synthesis which is fundamentally due to the inhibition against tyrosinase.

What is claimed is:
1. 1,3-diphenylpropane derivative represented by the following formula (I):

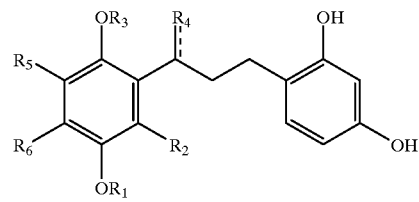

in which

-- represents double or single bond,

R$_1$ represents hydrogen or C$_1$-C$_{10}$ alkyl,

R$_2$ represents C$_1$-C$_5$ alkyl or C$_1$-C$_5$ alkoxyalkyl, or

R$_1$ and R$_2$ together represent a 5 to 6 membered heterocycle which can be substituted by C$_1$-C$_5$ alkyl and which contains oxygen as the hetero atom, R$_3$ represents hydrogen or C$_1$-C$_7$ alkyl, R$_4$ represents hydrogen, hydroxy, or oxo, and R$_5$ and R$_6$ independently of one another represent hydrogen or C$_1$-C$_5$ alkyl.

2. The compound of claim 1, wherein R$_1$ represents hydrogen, methyl or ethyl, R$_2$ represents methyl, or R$_1$ and R$_2$ together represent

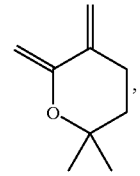

R$_3$ represents hydrogen or methyl, R$_4$ represents hydrogen or hydroxy, and R$_5$ and R$_6$ independently of one another represent methyl.

3. A process for preparing a compound represented by the following formula (Ia),

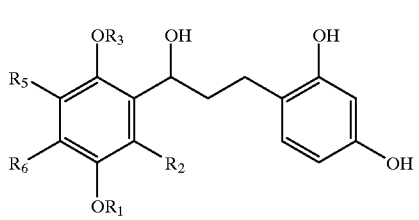

in which

R$_1$ represents hydrogen or C$_1$-C$_{10}$ alkyl,

R$_2$ represents C$_1$-C$_5$ alkyl or C$_1$-C$_5$ alkoxyalkyl, or

R$_1$ and R$_2$ together represent a 5 to 6 membered heterocycle which can be substituted by C$_1$-C$_5$ alkyl and which contains oxygen as the hetero atom, R$_3$ represents hydrogen or C$_1$-C$_7$ alkyl, R$_5$ and R$_6$ independently of one another represent hydrogen or C$_1$-C$_5$ alkyl, comprising the steps of:
reducing a compound represented by the following formula (IV),

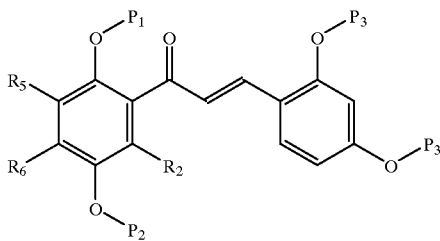

(IV)

in which

P$_1$ represents benzyl, methyl, ethyl, tetrahydropyranyl, methoxymethyl, methoxyethoxymethyl or p-methoxybenzyl, P$_2$ represents benzyl, methyl or ethyl P$_3$ represents benzyl, tetrahydropyranyl, methoxymethyl, methoxyethoxymethyl or p-methoxybenzyl, and R$_2$, R$_5$ and R$_6$ are as defined above, in a solvent to produce a compound represented by the following formula (V),

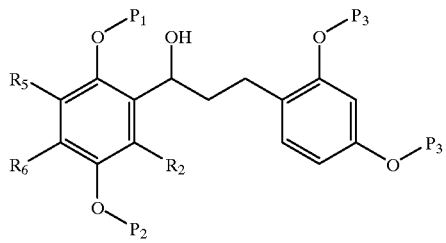

(V)

in which P$_1$, P$_2$ and P$_3$ are defined as above and R$_2$, R$_5$ and R$_6$ are as defined above; and then removing the protecting groups in the compound of formula (V).

4. The process of claim 3, wherein the reduction is carried out in a solvent selected from a group consisting of diethylether and tetrahydrofuran (THF) in the presence of lithium aluminum hydride(LAH).

5. The process of claim 4, wherein the reduction is carried out at temperatures ranging from −30 to 30° C.

6. A process for preparing a compound represented by the following formula (Ib),

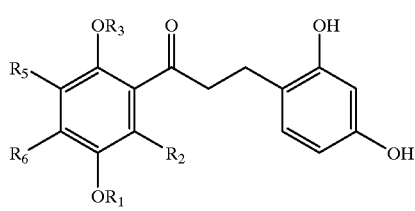

(Ib)

in which

R$_1$ represents hydrogen or C$_1$–C$_{10}$ alkyl,

R$_2$ represents C$_1$–C$_5$ alkyl or C$_1$–C$_5$ alkoxyalkyl, or

R$_1$ and R$_2$ together represent a 5 to 6 membered heterocycle which can be substituted by C$_1$–C$_5$ alkyl and which contains oxygen as the hetero atom, R$_3$ represents hydrogen or C$_1$–C$_7$ alkyl, R$_5$ and R$_6$ independently of one another represent hydrogen or C$_1$–C$_5$ alkyl, comprising the steps of:

hydrogenating the double bond in a compound represented by the following formula (IV),

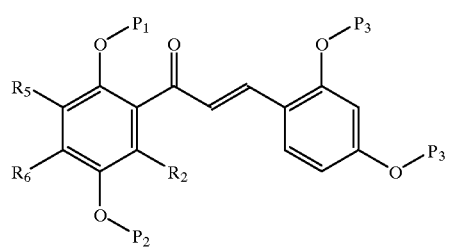

(IV)

in which

P$_1$ represents benzyl, methyl, ethyl, tetrahydropyranyl, methoxymethyl, methoxyethoxymethyl or p-methoxybenzyl, P$_2$ represents benzyl, methyl or ethyl P$_3$ represents benzyl, tetrahydropyranyl, methoxymethyl, methoxyethoxymethyl or p-methoxybenzyl, and R$_2$, R$_5$ and R$_6$ are as defined above, in a solvent to produce a compound represented by the following formula (V'),

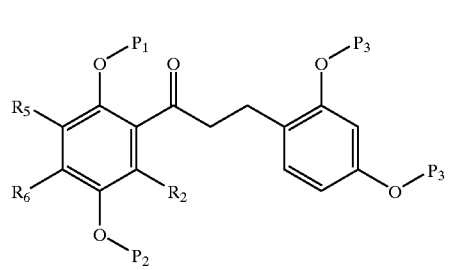

(V')

in which P$_1$, P$_2$ and P$_3$ are as defined above and R$_2$, R$_5$ and R$_6$ are as defined above; and then removing the protecting groups in the compound of formula (V').

7. The process of claim 6, wherein the solvent is ethylacetate.

8. The process of claim 6, wherein the protecting group is benzyl.

9. The process of claim 8, wherein the solvent is ethylacetate and the hydrogenation is carried out for 10 to 15 hours under normal temperature and pressures ranging from 2 to 4 atms.

10. The process of claim 8, wherein the solvent is a mixture of ethylacetate and a lower alcohol and the hydrogenation is carried out for 20 minutes to one hour under temperatures ranging from 35 to 55° C. and normal pressure.

11. A process for preparing a compound represented by the following formula (Ic),

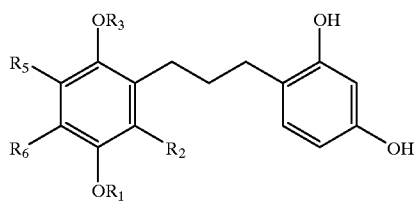

(Ic)

in which

R₁ represents hydrogen or $C_1$–$C_{10}$ alkyl,

R₂ represents $C_1$–$C_5$ alkyl or $C_1$–$C_5$ alkoxalkyl, or

R₁ and R₂ together represent a 5 to 6 membered heterocycle which can be substituted by $C_1$–$C_5$ alkyl and which contains oxygen as the hetero atom, R₃ represents hydrogen or $C_1$–$C_7$ alkyl, R₅ and R₆ independently of one another represent hydrogen or $C_1$–$C_5$ alkyl, comprising the steps of:
dehydrating a compound represented by the following formula (V),

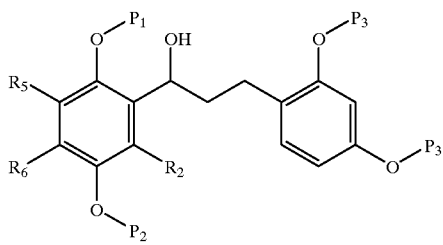

(V)

in which

P₁ represents benzyl, methyl, ethyl, tetrahydropyranyl, methoxymethyl, methoxyethoxymethyl or p-methoxybenzyl, P₂ represents benzyl, methyl or ethyl P₃ represents benzyl, tetrahydropyranyl, methoxymethyl, methoxyethoxymethyl or p-methoxybenzyl, and R₂, R₅ and R₆ are as defined above, in a solvent to produce a compound represented by the following formula (VI),

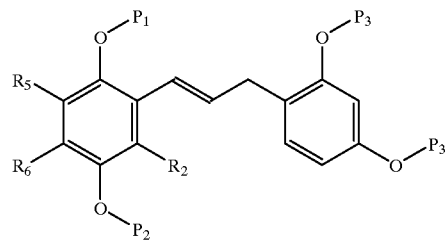

(VI)

in which P₁, P₂ and P₃ are as defined above and R₂, R₅ and R₆ are as defined above; and then
reducing and deprotecting the compound of formula (V) thus produced.

12. The process of claim 11, wherein the dehydration is carried out in a solvent selected from a group consisting of benzene, toluene and xylene in the presence of an acid selected from a group consisting of sulfuric acid, phosphoric acid and p-toluenesulfonic acid.

13. The process of claim 12, wherein the dehydration is carried out at temperatures ranging from 80 to 100° C.

14. The process of claim 6, wherein the protecting group is benzyl and the compound of formula (Ib) is produced by carrying out the hydrogenation and deprotection of the compound of formula (IV) in ethyl acetate or a solvent mixture of ethyl acetate and a lower alcohol.

* * * * *